United States Patent [19]

Doolin et al.

[11] Patent Number: 4,996,148

[45] Date of Patent: Feb. 26, 1991

[54] A80407 ANTIBIOTICS

[75] Inventors: Lawrence E. Doolin; Richard M. Gale, both of Indianapolis; Otis W. Godfrey, Greenwood; Robert L. Hamill, Greenwood; David F. Mahoney, Indianapolis; Raymond C. Yao, Carmel, all of Ind.

[73] Assignee: Eli Lilly and Company, Indianapolis, Ind.

[21] Appl. No.: 72,323

[22] Filed: Jul. 13, 1987

[51] Int. Cl.$^5$ .................. C12P 17/18; C12P 1/06; C12P 21/04; C12N 1/20

[52] U.S. Cl. ................... 435/119; 435/119; 435/252.1; 435/71.3; 435/74

[58] Field of Search ............ 435/119, 169, 254, 252.1, 435/71, 74

[56] References Cited

U.S. PATENT DOCUMENTS

| | | | |
|---|---|---|---|
| 2,990,329 | 6/1961 | Philip et al. | 167/65 |
| 3,067,099 | 12/1962 | McCormick et al. | 167/65 |
| 3,780,174 | 12/1973 | Hamill et al. | 424/118 |
| 4,083,964 | 4/1978 | Michel et al. | 424/118 |
| 4,322,406 | 3/1982 | Debono et al. | 424/118 |
| 4,456,593 | 6/1984 | Herrin et al. | 424/177 |
| 4,495,179 | 1/1985 | Hoehn et al. | 514/9 |
| 4,537,879 | 8/1985 | Hamill et al. | 514/9 |
| 4,542,018 | 9/1985 | Borghi et al. | 424/119 |
| 4,672,036 | 6/1987 | Bowie et al. | 435/254 |

OTHER PUBLICATIONS

Herrin et al., "Preparation of Biologically Active Ristocetin Derivatives: Replacement of the 1'-Amino Group," *J. Med. Chem.* 28, 1371–1375 (1985).

Sitrin et al., "Aridicins, Novel Glycopeptide Antibiotics, II, Isolation and Characterization," *J. Antibiotics* 38 (5), 561–571 (1985).

Mertz et al., "*Kibdelosporangium philippinensis Sp. Nov.* Iso lated From Soil", *Int. J. of Systematic Bacteriology*, 1988, Jul., pp 282–286, vol. 38, No. 3.

Shearer et al. (I), *J. of Antibiot.*, vol. 38, 1985, pp. 555–560.

Shearer et al. (II) *J. of Antibiot.*, vol. 39, 1986, pp. 1386–1406.

*Primary Examiner*—Elizabeth C. Weimar
*Assistant Examiner*—Irene Marx
*Attorney, Agent, or Firm*—Joseph A. Jones; Leroy Whitaker; Nancy J. Harrison

[57] ABSTRACT

New glycopeptide antibiotic A80407, comprising A80407A and A80407B, is produced by *Kibdelosporangium philippinensis* strains NRRL 18198, and NRRL 18199 or A80407-producing mutants of these strains. The A80407 antibiotics have excellent activity against Gram-positive bacteria, increase feed-utilization efficiency in monogastric and ruminant animals and improve weight gains in animals.

9 Claims, 4 Drawing Sheets

A80407 ANTIBIOTICS

SUMMARY OF THE INVENTION

This invention relates to antibiotic A80407 comprising individual components A80407A and A80407B and to their salts. Antibiotic A80407 is produced by culturing a new microorganism selected from *Kibdelosporangium philippinensis* strains NRRL 18198, NRRL 18199 or an A80407-producing mutant thereof under submerged aerobic fermentation conditions.

The A80407 antibiotics inhibit the growth of certain pathogenic microorganisms, particularly Gram-positive microorganisms. The A80407 antibiotics also promote weight gains and improve feed efficiency in monogastric and ruminant animals.

This invention also relates to a biologically purified culture selected from the *Kibdelosporangium philippinensis* strains NRRL 18198 and NRRL 18199, or an A80407-producing mutant thereof, which are useful for producing the A80407 antibiotics.

DESCRIPTION OF THE DRAWINGS

Infrared absorption spectra of the A80407 components A and B are shown in FIGS. 1-2 as follows.

DETAILED DESCRIPTION OF THE INVENTION

Although many beneficial antibiotics are available today, the need to find improved antibiotics for animal and human medicine continues.

This invention relates to a new group of glycopeptide antibiotics, the A80407 antibiotics. Previously known glycopeptides include vancomycin, ristocetin, actaplanin (A4696), teichoplanin, aridicin, A41030, A47934 and A35512. The A80407 antibiotics appear to be closest structurally to ristocetin.

In particular, this invention relates to new antibiotic A80407 comprising individual components A80407A and A80407B, to the individual components and to their salts, especially their pharmaceutically acceptable salts.

Antibiotic A80407 is produced by culturing a novel microorganism selected from *Kibdelosporangium philippinensis* NRRL 18198, NRRL 18199, or an A80407-producing mutant of these *K. philippinensis* strains. As those skilled in fermentation processes will recognize, the ratio of the components in antibiotic A80407 will vary, depending upon the conditions used. A80407A and A80407B are separated and isolated as individual compounds, as described infra.

In discussions of utility, the term "A80407 antibiotic" will denote a member selected from the group consisting of antibiotic A80407, its individual components A80407A and A80407B, and their pharmaceutically acceptable salts.

A80407 is soluble in water, dilute aqueous acid, dilute aqueous base and in mixtures of water and solvents such as methanol, ethanol, dimethylformamide, dimethyl sulfoxide, acetonitrile and acetone and the like.

The following paragraphs describe the physical and spectral properties of the A80407 components which have thus far been characterized.

A80407A

A80407A has the following characteristics:

Molecular Weight: 2145

Empirical Formula: $C_{97}H_{113}N_9O_{42}Cl_2$

FAB-MS(M+1): 2146

Figure 1:
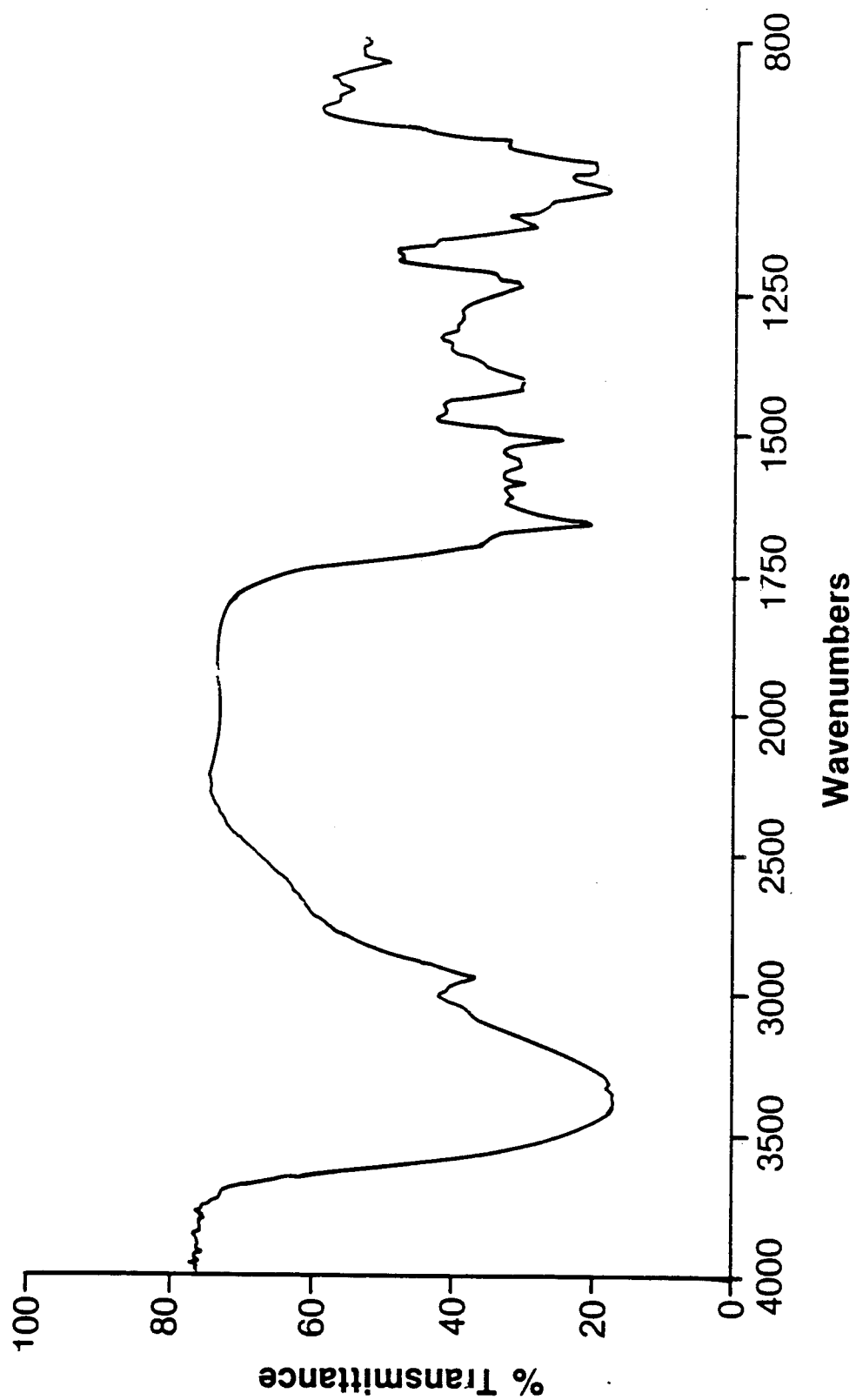
FIG. 1—A80407A (in KBr disk)

UV ($H_2O$) λmax: 277 nm ($\epsilon$ 6,880), shifts to 278 nm ($\epsilon$ 7,020) with acid and to 296 nm ($\epsilon$ 7,360) with base IR (KBr): 2990, 2987, 2974, 2970, 2966, 2936, 2934, 1689, 1656*, 1609, 1586*, 1558*, 1554, 1551, 1529, 1506*, 1473, 1457, 1420*, 1413, 1405*, 1342, 1308, 1296, 1292, 1283, 1232*, 1217, 1182, 1131*, 1063*, 1026, 1025*, 1016, 982 and 841 cm$^{-1}$ (see FIG. 1) *10 strongest absorptions pKa ($H_2O$): 4.3, 5.7, 8.0, 9.7

Rotation: $[\alpha]_{589}^{25°}$ −92.14° (c 1.1, $H_2O$)

A80407B

A80407B has the following characteristics:

Molecular Weight: 2145

Empirical Formula: $C_{97}H_{113}N_9O_{42}Cl_2$

FAB-MS(M+1): 2146

Figure 2:
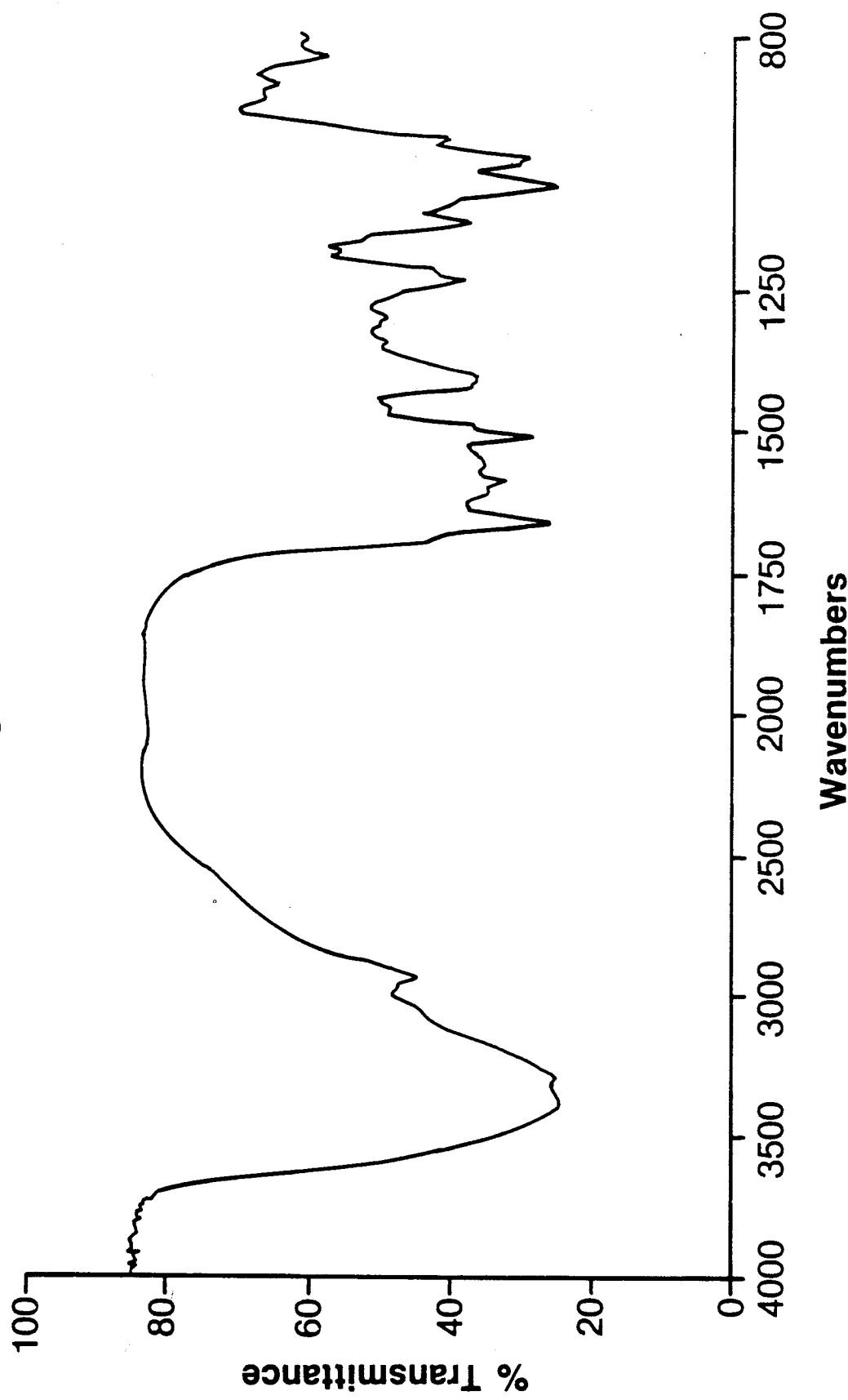
FIG. 2—A80407B (in KBr disk)

UV ($H_2O$) λmax: 275 nm ($\epsilon$ 6,630), shifts to 278 nm ($\epsilon$ 6,990) with acid and to 296 nm ($\epsilon$ 7,740) with base IR (KBr): 3090, 3075, 3019, 2999, 2973, 2934, 1657*, 1608*, 1587*, 1560, 1506*, 1491*, 1458, 1421*, 1407*, 1340, 1295, 1232, 1130, 1063*, 1026, 1015* and 981 cm$^{-1}$ (see FIG. 2) *10 strongest absorptions pKa ($H_2O$): 3.9, 5.1, 7.9, 9.6 Rotation: $[\alpha]_{589}^{25°}$ −68.12° (c 0.96, $H_2O$)

Elemental analysis of the A80407 components gave the following results:

|    | A80407B | A80407A | Calcd |
| --- | --- | --- | --- |
| C  | 54.52 | 50.53 | 54.24 |
| H  | 5.70  | 5.39  | 5.3   |
| N  | 5.57  | 5.21  | 5.87  |
| O  | 31.51 | 32.23 | 31.29 |
| Cl | 3.03  | 3.00  | 3.3   |

Comparative NMR, mass spectral and degradative studies indicate that A80407A and A80407B each contain rhamnose, three glucose and/or mannose sugar groups, and amino-sugars, which appear to be either vancosamine or ristosamine, or both.

A80407B and A80407A are stereoisomers. A80407B can be converted to A80407A under basic conditions, especially at pH levels of 8 or above. Since the conversion occurs at room temperature, isolation procedures aimed at recovering A80407B must be carried out at pH levels of 7 or below.

The A80407 components appear to constitute a new family of glycopeptides. The A80407 components are similar to ristocetin in general composition, differing mainly in chlorine content.

A80407 and its individual components A80407A and A80407B can react to form various salts. All such forms of these antibiotics are part of this invention. A80407 salts are useful, for example, for separating and purifying A80407. In addition, the salts have an improved solubility in water.

The term "pharmaceutically acceptable salts" is used herein to designate those salts which may safely be used in formulations to be administered to humans. The term "physiologically acceptable salts" is used to designate those salts which are suitable for administration to animals for veterinary medicine or growth promotion. These salts will generally also be pharmaceutically acceptable, but the range of salts useful in animals may vary somewhat.

A80407 salts are prepared using standard procedures for salt preparation. For example, A80407 can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable or physiologically acceptable acid addition salts are an especially preferred group of salts of this invention.

Antibiotic A80407 is produced by culturing an A80407-producing strain of *Kibdelosporangium philippinensis* under submerged aerobic conditions in a suitable culture medium until a recoverable amount of A80407 antibiotic activity is produced. The strains *K. philippinensis* NRRL 18198 and NRRL 18199, or A80407-producing mutant of these strains, are examples of suitable cultures. The antibiotic can be recovered using various isolation and purification procedures understood in the art.

This invention also relates to a biologically purified culture of a microorganism selected from *Kibdelosporangium philippinensis* NRRL 18198, *Kibdelosporangium philippinensis* NRRL 18199 or an A80407-producing mutant of these strains. These microorganisms are useful because they produce antibiotic A80407. For convenience in the discussion which follows, the NRRL 18198 strain has been designated culture A80407 and the NRRL 18199 strain has been designated culture A80407.4.

Culture A80407 was isolated from a soil sample from the Philippines. Culture A80407.4 was obtained from culture A80407 by chemical mutagenesis.

Cultures A80407 and A80407.4 have been deposited and made part of the stock culture collection of the Midwest Area Northern Regional Research Center, Agricultural Research Service (NRRL), United States Department of Agriculture, 1815 North University Street, Peoria, Ill., 61604, from which they are available to the public under the accession numbers NRRL 18198 (A80407, the parent strain) and NRRL 18199 (A80407.4, the mutant strain).

Taxonomic studies of cultures A80407 and A80407.4 were carried out by Frederick P. Mertz of the Lilly Research Laboratories. Based on these studies, the new organisms are classified as strains of *Kibdelosporangium philippinensis sp. nov*. This classification is based on simultaneous laboratory comparisons and examination of published descriptions; [B. A. Bowie, et al, "Antibiotics Produced by *K. aridum* Shearer," U.S. Pat. No. 4,548,974 (1985); M. C. Shearer, P. M. Colman, R. M. Ferrin, T. J. Nisbet, and C. H. Nash III, "New Genus of the *Actinomycetales: Kibdelosporangium aridum* gen. nov., sp. nov.," *Int. J. Syst. Bacteriol.* 36:47–54 (1986); and M. C. Shearer, A. J. Giovenella, S. F. Grappel, R. D. Hedde, R. J. Mehta, Y. K. Oh, C. H. Pan, D. H. Pitkin, and L. J. Nisbet, "Kibdelins, Novel Glycopeptide Antibiotics I. Discovery, Production, and Biological Evaluation," *J. Antibiot.* 39:1386–1394 (1986).

Methods Used

The methods followed were those recommended by the International Streptomyces Project (ISP) for the characterization of Streptomyces species [E. B. Shirling and D. Gottlieb, "Methods for Characterization of Streptomyces Species," *Int. J. Syst. Bacteriol.* 16: 313–340 (1966)].

Methods recommended by Gordon et al. [R. E. Gordon, D. A. Barnett, J. E. Handerhan, and C. H. Pang, "*Nocardia coeliaca, Nocardia autotrophica,* and the Nocardin Strain," *Int. J. Syst. Bacteriol.* 24, (1), 54–63 (1974)] were followed for the majority of physiological tests.

ISCC-NBS Centroid Color Charts (National Bureau of Standards, "ISCC-NBS Centroid Color Charts Standard Sample No. 2106," U.S. Department of Commerce, Washington, D.C., 1958) and the Color Harmony Manual (Color Harmony Manual, 4th ed. Container Corporation of America, 1958, Chicago, Ill.) were used to assign color names to the reverse side and aerial spore mass, respectively. Morphology was studied using an optical light microscope. A scanning electron microscope (SEM) was used to study the spore surface ornamentation.

Melanoid pigment production (chromogenicity) was determined with ISP No. 1 (tryptone-yeast extract broth), ISP No. 6 (peptone-yeast extract iron agar), and ISP No. 7 (tyrosine agar).

The isomer of diaminopimelic acid (DAP) and the carbohydrates in hydrolysates of whole cells were established by the chromatographic methods of Becker et. al. [B. Becker, M. P. Lechevalier, R. E. Gordon, and H. A. Lechevalier, "Rapid Differentiation Between *Nocardia* and *Streptomyces* by Paper Chromatography of Whole-Cell hydrolysates," *Appl. Microbiol.* 12:421–423 (1964)] and of Lechevalier [M. P. Lechevalier, "Identification of Aerobic Actinomycetes of Clinical Importance," *J. Lab. Clin. Med.* 71:934–944 (1968)].

Mycolic acids were determined by a method based on techniques described by Minnikin [D. E. Minnikin, I. G. Hutchinson and A. B. Caldicott, "Thin-layer Chromatography of Methanolysates of Mycolic Acid-Containing Bacteria," *J. Chromatography* 188:221–233 (1980)].

Phosphatase and urease were determined by methods described by Blazevic (D. J. Blazevic and G. M. Ederer, "Principles of Biochemical Tests in Diagnostic Microbiology," John Wiley and Sons, Inc., New York, 1975, p. 136). Gelatin liquefaction was used for the determination of proteinase activity.

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch agar) plates (Blazevic and Ederer, supra).

Allantoin decomposition was measured by the method of Kurup [P. Y. Kurup and J. A. Schmitt, "Numerical Taxonomy of Nocardia," *Can. J. Microbiol.* 19:1035-1048 (1973)].

Phospholipids were extracted with $CHCl_3$ and examined by TLC against phosphatidyl standards, visualizing with molybdenum spray.

Fatty acid methyl esters were analyzed by GLC on a Hewlett Packard 5898A computer-controlled gas chromatograph.

Protein analysis was performed with polypeptide banding patterns obtained by sodium dodecyl sulfate polyacrylamide gel electrophoresis (SDS-PAGE). A computer driven system matched profiles and provided statistical comparisons.

Cultural Characteristics

The A80407 and A80407.4 cultures grew on both complex and defined media. Aerial hyphae and sporangium-like structures were produced on most media. ISP No. 4 and tomato paste-oatmeal (TPO) agar media supported the best substrate and aerial hyphae development. The aerial spore mass color was white; the reverse color was generally pale yellow to orange yellow. Soluble pigments were occasionally produced.

The main cultural difference between the two strains was observed on glucose-asparagine agar. Strain A80407 produced some aerial hyphae and sporangium-like structures, but A80407.4 did not. In addition, A80407.4 produced a reddish-orange soluble pigment, but A80407 did not.

The cultural characteristics observed are summarized in Table I.

TABLE I

| Cultural Characteristics of A80407 & A80407.4[a] | | | |
|---|---|---|---|
| | | A80407 | A80407.4 |
| ISP 2 | G: | Abundant | Abundant |
| | R: | 74.s.yBr | 55.s.Br. |
| | Am: | Fair: a White | Fair: b White |
| | Sp: | Light brown | Dark brown |
| ISP 3 | G: | Good | Good |
| | R | 89.p.Y. | 89.p.Y |
| | Am: | Good: a White | Good: a White |
| | Sp: | None | None |
| ISP 4 | G: | Abundant | Good |
| | R: | 89.p.Y | 89.p.Y |
| | Am: | Abundant: a White | Good: a White |
| | Sp: | None | None |
| ISP 5 | G: | Good | Good |
| | R: | 92.y White | 70.l.OY |
| | Am: | Fair: a White | Fair: a White |
| | Sp: | None | None |
| ISP 7 | G: | Good | Good |
| | R: | 71.m.OY | 71.m.OY |
| | Am: | Fair: a White | Fair: a White |
| | Sp: | Very light brown | Very light brown |
| Calcium Malate | G: | Fair | Fair |
| | R: | 70.l.OY | 70.l.OY |
| | Am: | None | None |
| | Sp: | None | None |
| Czapek's | G: | Good | Good |
| | R: | 89.p.Y. | 89.p.Y. |
| | Am: | Good: a White | Good: a White |
| | Sp: | None | None |
| GYEA[b] | G: | Good | Good |
| | R: | 71.m.OY | 71.m.OY |
| | Am: | None | None |
| | Sp: | Light reddish orange | Light reddish orange |
| Glucose-Asparagine | G: | Good | Good |
| | R: | 71.m.OY | 54.br.O |
| | Am: | Poor: a White | None |
| | Sp: | None | Reddish-orange |
| Nutrient Agar | G: | Fair | Fair |
| | R: | 71.m.OY | 71.m.OY |
| | Am: | Poor: a White | Trace |
| | Sp: | None | None |
| TPO | G: | Abundant | Abundant |
| | R: | 77.m.yBr | 75.deep yBR |
| | Am: | Good: a White to Gray | Good: a White to Gray |
| | Sp: | None | None |
| TWA[c] | G: | Fair | Fair |
| | R: | 92.y White | 92.y. White |
| | Am: | Fair: a White | Fair: a White |
| | Sp: | None | None |

[a]G = growth; R = reverse; Am = aerial mycelia; Sp = soluble pigment
[b]GYEA = glucose yeast extract agar
[c]TWA = tap water agar

Morphological Characteristics

Both A80407 and A80407.4 had an extensive substrate mycelium. Their aerial hyphae produced long chains of spores. These spores were long cylindrical rods with a smooth surface, and averaged 1.6×0.4 μM in size.

Many sporangium-like structures were observed beneath the long spore chains. They were borne apically on aerial hyphae, were round, ranged from 1–10 μM in size, and had a rugose surface. No motile spores were observed. When grown under submerged shaken conditions, strain A80407.4 had a tendency toward fragmentation. This tendency was not observed in A80407.

Physiological Characteristics

Both A80407 and A80407.4 produced acid from: D-arabinose, cellobiose, fructose, galactose, glucose, glycerol, inositol, lactose, maltose, mannitol, mannose, melibiose, L-rhamnose, ribose, trehalose and xylose. Acid was not produced from: adonitol, L-arabinose, cellulose, dextrin, dulcitol, ethanol, erythritol, glycogen, inulin, raffinose, salicin, sorbitol, sorbose, xylitol and a-methyl D-glucoside. Culture A80407 produced acid from melezitose and sucrose; A80407.4 did not. Both cultures utilized acetate, butyrate, citrate, formate, lactate, malate, oxalate, propionate, pyruvate and succinate. They did not utilize benzoate or tartrate.

Both A80407 and A80407.4 decomposed: casein, calcium malate, elastin, hypoxanthine, testosterone, tyrosine and urea. They did not decompose: adenine, allantoin, guanine, starch and xanthine. Culture A80407 decomposed esculin and hippurate; A80407.4 did not.

Both cultures produced catalase, $H_2S$ and phosphatase. Both hydrolyzed milk, liquefied gelatin, produced melanoid pigments from ISP No. 1 and ISP No. 6, but not from ISP No. 7, tolerated levels of NaCl up to 2% and grew in a temperature range of 20°-40° C.

Neither culture was resistant to lysozyme. A80407 reduced nitrate to nitrites, but A80407.4 did not.

The cultures had an identical antibiotic resistance patterns. They were resistant to 30 μg cephalothin, 2 μg lincomycin, 15 μg oleandomycin, 10 units penicillin G, 10 μg tobramycin, 30 μg vancomycin, 30 μg nalidixic acid, 300 units polymixin B, 5 μg trimethoprim and 300 units of sulfadiazine. They were sensitive to 10 units bacitracin, 10 μg gentamycin, 30 μg neomycin, 5 μg rifampin, 10 μg tetracycline, 30 μg chloramphenicol, 15 μg erythromycin, 30 μg novobiocin and 3 μg mandelamine.

Cell-Wall Analysis

Hydrolyzed whole cells contained meso-diaminopimelic acid, galactose, glucose, mannose, arabinose and ribose. An unknown spot having an $R_{f(ribose)} = 0.15$ was observed for both cultures. No madurose was detected.

Phosphatidylethanolamine was observed from whole cell extracts. No mycolic acids were seen. Thus, A80407 has type IV cell walls [M. P. Lechevalier and H. Lechevalier, "Chemical Composition as a Criterion in the Classification of Aerobic Actinomycetes," *Int. J. Syst. Bacteriol.* 20:435-443 (1970)], a type A sugar pattern (Lechevalier and Lechevalier, supra), and a type P II phospholipid composition [M. P. Lechevalier, C. DeBievre, and H. A. Lechevalier, "Chemotaxonomy of Aerobic Actinomycetes: Phospholipid Composition," *Biochem. Syst. Ecol.* 5:249-260 (1977)], respectively. Attempts to extract and identify menaquinones were unsuccessful.

Identity of Strain A80407

The chemotaxonomic properties, general cultural characteristics, and especially the presence of sporangium-like structures are consistent with the assignment of A80407 to the new genus *Kibdelosporangium* Shearer, Colman, Ferrin, Nisbet, and Nash (Shearer et al., *Int. J. Syst. Bacteriol.*, supra)

Simultaneous laboratory comparisons were made between A80407 and the type strain of *Kibdelosporangium aridum* (ATCC 39323). A literature comparison was made with *K. aridum* subsp. *largum* (ATCC 39922) (Shearer et al., *J. Antibiot.*, supra). Significant differences were observed.

Figure 3:
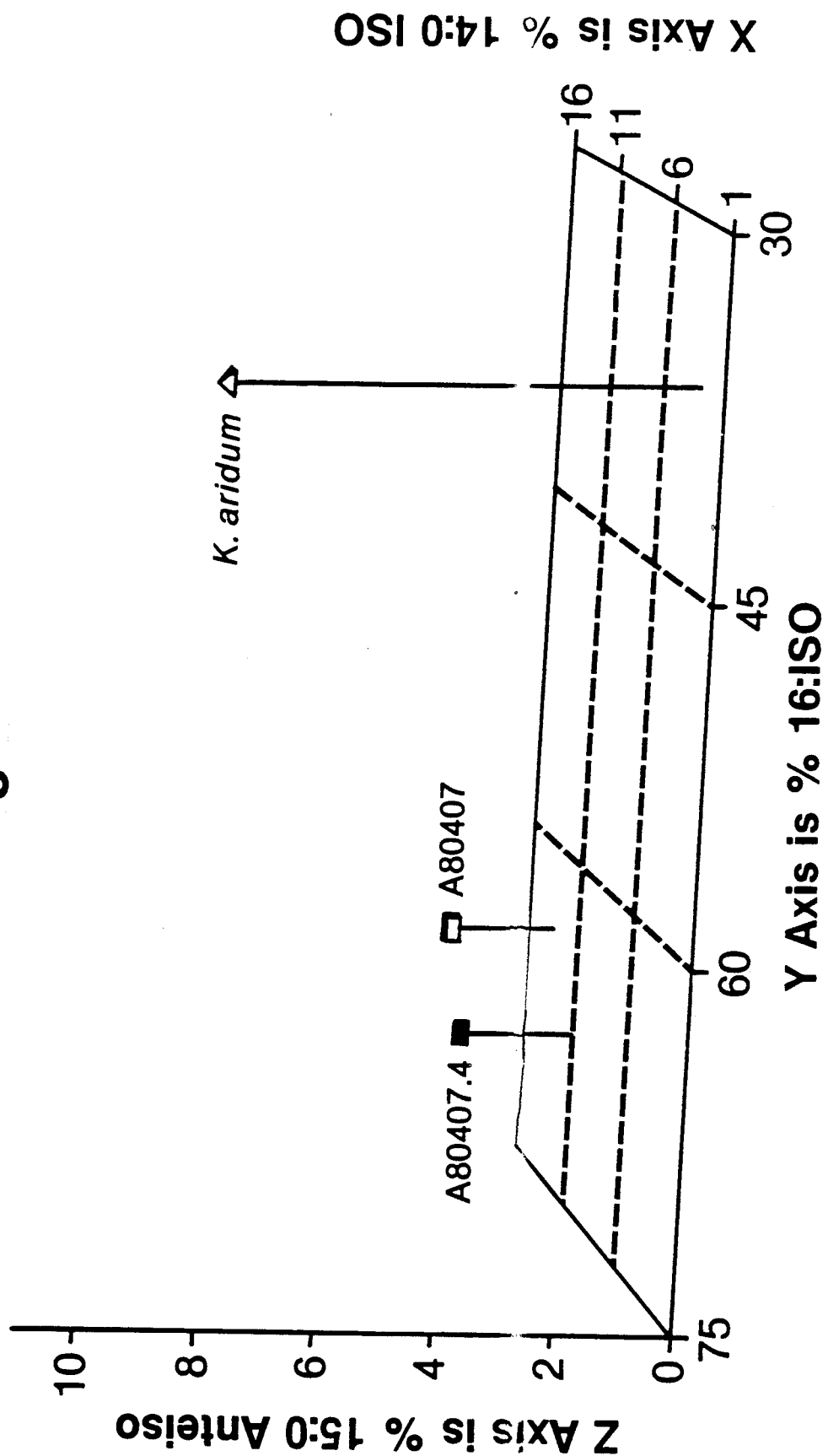
FIG. 3 is a three dimensional plot showing % total amount of named fatty acids between 9-20 carbon length found on fatty acid analysis of *Kibdelosporangium philippinensis* strains NRRL 18198 and NRRL 18199 and *K. aridum* ATCC 39323.

Fatty acid analysis was done on the two A80407 strains and the type strain *K. aridum*, using lyophilized whole cells grown under identical conditions. As FIG. 3 shows, the A80407 and A80407.4 strains cluster distinct from *K. aridum*. In addition, *K. aridum* has two fatty acids which are not present in A80407 or A80407.4: the trans 16:1 and anteiso 17:1. These differences should not occur within the same species.

Figure 4:
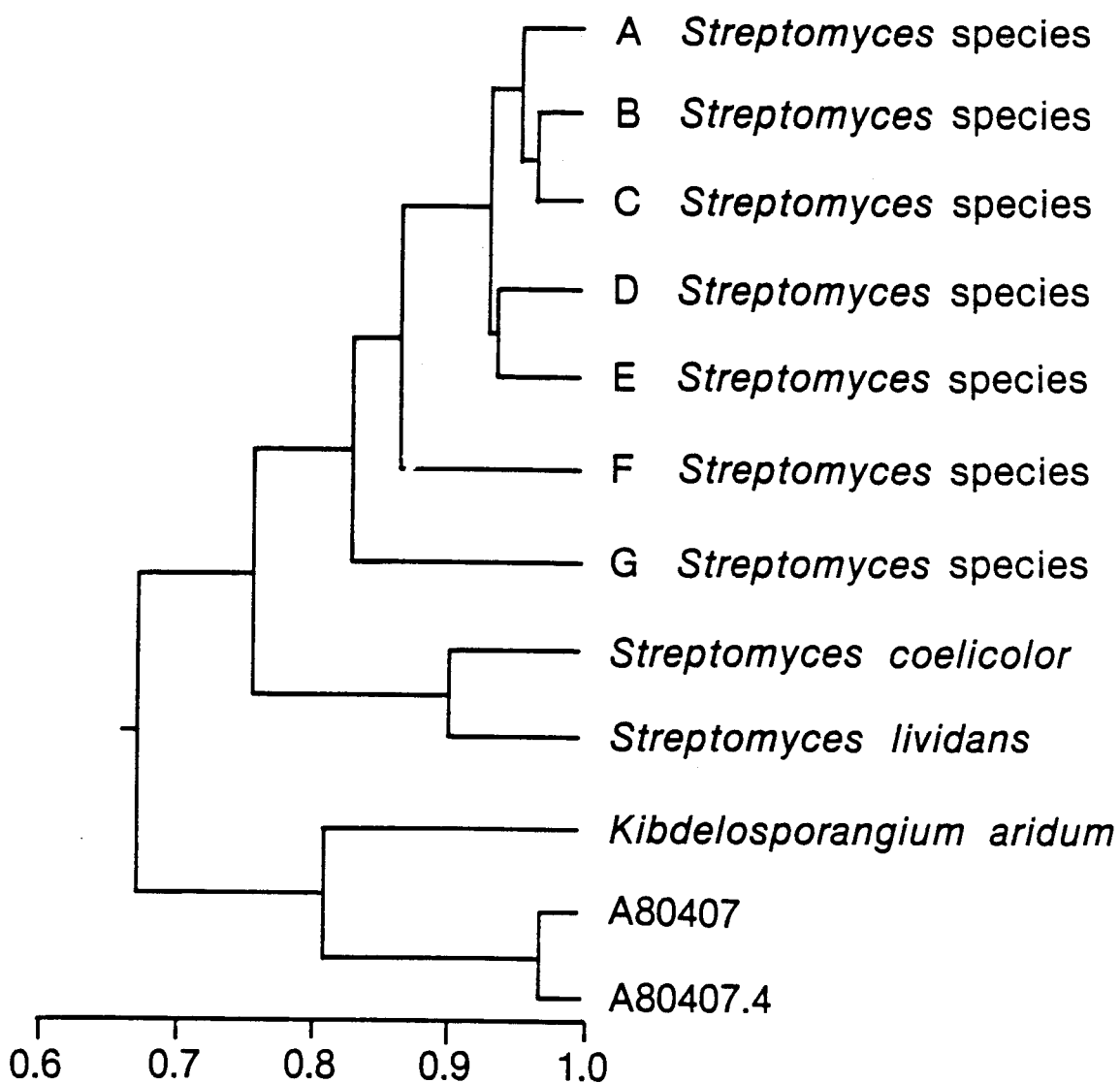
FIG. 4 is a dendogram showing protein PAGE profile relationships among 12 Actinomycete strains. The dendogram was constructed using coefficients of correlation (r) for *K. philippinensis* strains NRRL 18198, and NRRL 18199 and *K. aridum* ATCC 39323. Clustering was done by the unweighted pair-group method with average linkage (UPGMA).

Protein polyacrylamide gel electrophoresis (PAGE) gave a pattern of the polypeptide bands. This microbial fingerprint allows for computerized matching of protein patterns. As FIG. 4 shows, the A80407 and A80407.4 strains cluster at R=0.96, and the *K. aridum* strain clusters at R=0.81. This dendogram suggests that the three strains belong to the same genus but are different species. When 108 physiological characters were used to calculate the coefficient of similarity using the Jaccard coefficient [P. H. A. Sneath, "The Application of Computers to Taxonomy", *J. Gen. Microbiol.*, 17:201-226 (1957), the quotient was 0.81, i.e. identical to the protein banding coefficient.

Table II summarizes taxonomic comparisons between strain A80407 and *K. aridum* ATCC 39323.

TABLE II

Taxonomic Comparison of Strain A80407 with *K. aridum* ATCC 39323

| Characteristic | A80407 | ATCC 39323 |
|---|---|---|
| Formation of aerial mycelia | Good | Poor |
| Formation of sporangium-like structures | Profuse | Sparse |
| Reverse color | Orange-yellow | Off-white |
| Soluble pigments | Occasionally | Rarely |
| Crystals produced | − | + |
| Cell wall components: | | |
| unknown spot | + | − |
| madurose | − | + |
| L-rhamnose | − | + |
| Utilization of: | | |
| L-arabinose | − | + |
| dextrin | − | + |
| glycogen | − | + |
| α-Me-D-glucoside | − | + |
| D-melezitose | + | − |
| D-raffinose | − | + |
| Resistance to: | | |
| Bacitracin - 10 units | − | + |
| Gentamcin - 10 μg | − | + |
| Oleandomycin - 15 μg | + | − |
| Streptomycin - 10 μg | − | + |
| NaCl tolerance - % | 2 | ≧7 |
| Temperature range - °C. | 20-40 | 5-45 |
| Nitrate reduction | + | − |
| Allantoin decomposed | − | + |
| Guanine hydrolyzed | − | + |
| Peptonization of milk | − | + |
| Glycopeptide antibiotic produced | Ristocetin-like | Ardacin |
| Size of aerial spores - μm | 0.4 × 1.6 | 0.4 × 2.8 |
| Size of sporangia - μm | 1-8 | 9-22 |
| Fatty acid analysis: | | |
| ISO 14:0 - % | 13.4 | 2.8 |
| ISO 16:0 - % | 63.9 | 36.7 |
| Anteiso 15:0 - % | 1.9 | 8.0 |
| Trans 16:1 | − | + |
| Anteiso 17:1 | − | + |

*Kibdelosporangium aridum* subsp. *largum* (ATCC 39922) was unavailable for comparative studies. Therefore, fatty acid analysis and protein profile relationships could not be made. The published description (Shearer et al., *J. Antibiot., supra*) indicates that there are significant differences between *K. aridum* subsp. *largum* and A80407. These differences are summarized in Table III.

TABLE III

Differences Between A80407 and
*K. aridum* subsp *largum* ATCC 39922

| Characteristic | A80407 | ATCC 39922 |
| --- | --- | --- |
| NaCl tolerance - % | 2 | 7 |
| Temperature range - °C. | 20–40 | 15–42 |
| Peptonization of milk | − | + |
| Hydrolysis of guanine | − | + |
| Hydrolysis of allantoin | − | + |
| Reduction of nitrate | + | − |
| Utilization of: | | |
| α-arabinose | − | + |
| dextrin | − | + |
| glycogen | − | + |
| α-methyl-D-glucoside | − | + |
| raffinose | − | + |
| salicin | − | + |

These comparisons indicate that strain A80407 is unlike the described species of Kibdelosporangium. A80407 strain is, therefore, a new species for which the name *K. philippinensis* sp. nov. has been tentatively selected. The type strain would be A80407.

A80407.4, which is a derived mutant of A80407, is distinguished from the parent strain by the characteristics shown in Table IV:

TABLE IV

Differences Between Strains A80407
and A80407.4

| Characteristic | A80407 | A80407.4 |
| --- | --- | --- |
| Properties on glucose - asparagine agar: | | |
| aerial hyphae | + | − |
| sporangium-like structures | + | − |
| reddish-orange soluble pigment | − | + |
| Utilization of: | | |
| D-melizitose | + | − |
| sucrose | + | − |
| Hydrolysis of: | | |
| esculin | + | − |
| hippurate | + | − |
| Reduction of nitrate | + | − |

The genus Kibdelosporangium is not currently listed in the Approved Lists of Bacterial Names [V. B. D. Skerman, V. McGowan, and P. H. A. Sneath (eds.), "Approved Lists of Bacterial Names," *Int. J. Syst. Bacteriol* 30:225–420 (1980)] because of its recent discovery. It has, however, been validly published in the official Journal and is, therefore, an accepted taxon.

As is the case with other organisms, the characteristics of the A80407-producing cultures of this invention, *Kibdelosporangium philippinensis* strains NRRL 18198 and NRRL 18199, are subject to variation. Thus, progeny of these strains, e.g., mutants, may be obtained by methods known in the art. For example, spontaneous mutants can be obtained by natural selection and induced mutants can be obtained by treatment with various known physical and chemical mutagens such as ultraviolet light, X rays, gamma rays and chemicals such as N-methyl-N'-nitro-N-nitrosoguanidine. Mutants of the *Kibdelosporangium philippinensis* strains NRRL 18198 and NRRL 18199 which retain the characteristic of A80407 production are part of this invention.

The culture medium used to grow the *Kibdelosporangium philippinensis* cultures can be any one of a number of media. For economy in production, optimal yield, and ease of product isolation, however, certain culture media are preferred. Thus, for example, preferred carbohydrate sources in large-scale fermentation are glucose, glycerol and soluble starch, although soybean flour, ribose, xylose, fructose, galactose, mannose, mannitol, and the like can also be used.

A preferred nitrogen source is enzyme-hydrolyzed casein, although yeast extract, ammonium salts, acid-hydrolyzed casein, beef extract, and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism.

If foaming is a problem, small amounts (i.e. 0.2 mL/L) of an antifoam agent such as polypropylene glycol may be added to large scale fermentation media.

For production of substantial quantities of the A80407 antibiotics, submerged aerobic fermentation in tanks is preferred. Small quantities of the antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

The A80407 antibiotics are produced by the A80407-producing organisms when grown at temperatures between about 25° and about 34° C. An optimum temperature for A80407 production appears to be about 30° C.

As is customary in submerged aerobic culture processes, sterile air is blown into the vessel from the bottom while the medium is stirred with conventional turbine impellors. In general, the aeration and agitation rates should be sufficient to maintain the level of dissolved oxygen at or above 20%, and preferably above 50%, of saturation.

Production of the A80407 antibiotics can be followed during the fermentation by testing samples of the broth for antibiotic activity against organisms known to be sensitive to the antibiotic. One useful assay organism is *Bacillus subtilis* ATCC 6633. The bioassay is conveniently performed by the agar-well plate test.

Following their production under submerged aerobic fermentation conditions, the A80407 antibiotics can be recovered from the fermentation medium by methods used in the art. The antibiotic activity produced during fermentation of the A80407-producing organisms occurs mainly in broth. Maximum recovery of A80407 is accomplished, therefore, by initially filtering the medium to separate the broth from the mycelial mass.

A80407 can be recovered from the filtered broth by a variety of techniques. A preferred technique involves adjusting the whole broth to a pH of about 6 or below before filtering and adsorbing the filtered broth onto a macroreticular resin, e.g. Diaion HP-20 and Amberlite XAD-4, and eluting the active material with a suitable solvent, such as water:acetonitrile (9:1) containing 1% acetic acid, to give antibiotic A80407. The active material can also be eluted with water:isopropanol or water-:isopropanol mixtures containing small amounts of acid.

A80407 can be separated into individual components A80407A and A80407B by similar procedures. A preferred separation procedure involves reverse-phase silica-gel ($C_{18}$ or $C_8$) chromatography.

Alternatively, the culture solids, including medium constituents and mycelium can be used without extraction or separation, but preferably after removal of water, as a source of A80407. For example, after production of A80407, the whole fermentation broth can be dried by lyophilization, by drum-drying, or by azeotropic distillation and drying. The dried broth can then be mixed directly into feed premix.

The A80407 antibiotics are antibacterial agents. In particular, they have excellent in vivo activity against Gram-positive pathogenic bacteria. A80407B is comparable in activity to the commercially useful antibiotic vancomycin.

The minimal inhibitory concentrations (MIC's) at which the A80407 antibiotics inhibit certain bacteria are given in Table V. The MIC's in Table V were determined by standard agar-dilution assays.

TABLE V

In Vitro Antibacterial Activity of the A80407 Antibiotics

| Test Organism | MIC (μg/mL) | |
|---|---|---|
| | A80407A | A80407B |
| Staphylococcus aureus X1.1 | 8 | 8 |
| Staphylococcus aureus V41[a] | 8 | 8 |
| Staphylococcus aureus X400[b] | 16 | 8 |
| Staphylococcus aureus S13E | 8 | 4 |
| Staphylococcus epidermidis 270 | 8 | 4 |
| Staphylococcus epidermidis 222 | 8 | 4 |
| Streptococcus pyogenes C203 | 2 | 0.25 |
| Streptococcus pneumoniae Park I | 1 | 0.125 |
| Streptococcus faecalis X66 | 16 | 1 |
| Streptococcus faecalis 2041 | 16 | 2 |
| Haemophilus influenzae C.L.[c] | 32 | >128 |
| Haemophilus influenzae 76[d] | 16 | >128 |
| Gram Negative | >128 | >128 |

[a]Penicillin-resistant strain;
[b]Methicillin-resistant strain;
[c]Ampicillin-sensitive strain;
[d]Ampicillin-resistant strain;

Another aspect of the antimicrobial activity of the A80407 compounds is their activity against anaerobic bacteria This activity is illustrated in Table VI, which summarizes the activity of A80407B against certain anaerobic bacteria, as determined by standard agar-dilution assay. End points were read after 24-hour incubation.

TABLE VI

Activity of A80407B Against Anaerobic Bacteria

| Anaerobic Bacteria | MIC (μg/mL)[a] |
|---|---|
| Clostridium difficile 2994 | 2 |
| Clostridium perfringens 81 | 1.0 |
| Clostridium septicum 1128 | 2 |
| Eubacterium aerofaciens 1235 | >128 |
| Peptococcus asaccharolyticus 1302 | 128 |
| Peptococcus prevoti 1281 | 128 |
| Peptostreptococcus anaerobius 1428 | >128 |
| Peptostreptococcus intermedius 1264 | 8 |

TABLE VI-continued

Activity of A80407B Against Anaerobic Bacteria

| Anaerobic Bacteria | MIC (μg/mL)[a] |
|---|---|
| Propionibacterium acnes 79 | 1.0 |
| Bacteroides fragilis (3 species) | >128 |
| Bacteroides thetaiotaomicron 1438 | >128 |
| Bacteroides melaninogenicus 1856/28 | >128 |
| Bacteroides vulgatis 1211 | >128 |
| Bacteroides corrodens 1874 | >128 |
| Fusobacterium symbiosum 1470 | 32 |
| Fusobacterium necrophorum 6054A | >128 |

[a]MIC determined by the agar-dilution method; endpoints were read after 24-hours incubation.

The A80407 antibiotics have also shown in vivo antimicrobial activity against experimentally-induced infections in laboratory animals. When two doses of est compound were administered to mice experimentally infected with the test organism, the activity observed as measured as an $ED_{50}$ value effective dose in mg/kg o protect 50% of the test animals: see Warren Wick, et al., *J. Bacteriol.* 81, 233-235 (1962). ED50 values observed for the A80407 components are given in Table VII.

TABLE VII

In Vivo Activity of A80407 Antibiotics

| | $ED_{50}$ Value[a] | | |
|---|---|---|---|
| Compound | Staphylococcus aureus | Streptococcus pyogenes | Streptococcus pneumoniae |
| A80407A | 10-13.59 | 6.23 | 12.4 |
| A80407B | 1.39 | <0.31 | 0.51 |

[a]mg/kg × 2; doses administered subcutaneously to mice 1 and 4 hours post-infection Furthermore, the A80407 antibiotics have exhibited beneficial effects on feed utilization in ruminants. The efficiency of feed use can be monitored by observing the production and concentration of propionate compounds in the rumen using the method described by Arthur P. Raun in U.S. Pat. No. 3,794,732 see especially Example 5). Table VIII shows the effect of A80407B on rumen energy fermentation in vitro. As this test demonstrates, A80407B increases propionates and decreases methane production significantly. Compounds having such effects improve feed-utilization efficiency in ruminants having functional rumens.

TABLE VIII

Effect of A80407B on Rumen Energy Fermentation in Continuous Culture[1]

| Treatment | Dosage (mg/L) | Production Rate, mM/Day | | | | |
|---|---|---|---|---|---|---|
| | | Acetic Acid | Propionic Acid | Butyric Acid | TVFA[2] | CH4 |
| Control | — | 35.4 | 11.4 | 11.8 | 58.6 | 5.0 |
| A80407B | 1 | 35.8 | 12.5 | 11.7 | 60.0 | 4.2 |
| A80407B | 2 | 34.7 | 14.7 | 10.9 | 60.3 | 3.6 |
| SEM[3] | | .4 | .7 | .3 | .5 | .5 |

[1]Two flasks for each treatment group, observed daily during an eight-day treatment period
[2]Total volatile fatty acids
[3]Standard error of the mean The A80407 antibiotics are also useful as growth-promoting agents in animals. For example, the A80407 antibiotics promote growth in both monogastric animals, such as swine and poultry, and in ruminants, such as cattle and sheep. This beneficial effect has been demonstrated by the activity of A80407A and A80407B in poultry growth studies. In these studies, the test compound is added to the feed of broiler chicks. Five replicates of seven birds for each of two time replicates are used. The animals are treated for 11-13 days. The results of these studies are summarized in Table IX.

TABLE IX

| | Effect of A80407 on Poultry Growth | | | | |
|---|---|---|---|---|---|
| Treatment | Dosage (g/ton) | Weight Gain (g) | Percent Wt. Gain | Feed/ Gain | Percent Feed/Gain |
| Control[1] | — | 314 | — | 1.746 | — |
| A80407A[1] | 20 | 354 | 12.7 | 1.683 | 3.6 |
| Control[2] | — | 212 | — | 1.968 | — |
| A80407B[2] | 20 | 321 | 51.4 | 1.619 | 17.7 |

[1] 13 days on treatment
[2] 11 days on treatment

Pharmaceutical and veterinary formulations of the A80407 antibiotics are also part of this invention. In the discussion of pharmaceutical uses in humans, an "A80407 antibiotic" refers to a purified A80407 component or a pharmaceutical acceptable salt of a component. For veterinary uses, an "A80407 antibiotic" refers to antibiotic A80407, an A80407 component or mixture of components or their physiologically acceptable salts.

In one aspect, an A80407 antibiotic, preferably in the form of a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like.

The compositions comprising an A80407 antibiotic will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of an A80407 antibiotic which is effective for this purpose. In general, an effective amount of A80407 antibiotic is a dose between about 0.5 and about 100 mg/kg. A preferred dose is from about 1 to about 60 mg/kg of active compound. A typical daily dose for an adult human is from about 50 mg to about 1.0 g.

In practicing this method, the antibiotic can be administered in a single daily dose or in multiple doses per day. The treatment regime may require administration over extended periods of time, e.g., for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggyback method of IV infusion can also be used.

This invention further relates to veterinary compositions adapted either to (1) improve feed-utilization efficiency or (2) promote growth in animals. These compositions comprise a carrier, such as a feed ration, and an effective amount of an A80407 antibiotic for the intended purpose. In general an effective amount of A80407 antibiotic for these purposes is in the range from 2.5 to 100 grams of antibiotic per ton.

For veterinary uses, an A80407 antibiotic can also be administered to animals either orally or parenterally. The most practical way to administer the A80407 antibiotics is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80407 antibiotic directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing an A80407 compound.

The A80407 antibiotics may be formulated for parenteral administration by methods recognized in the veterinary pharmaceutical art. Effective injectable compositions containing the A80407 antibiotics may be in either suspension or solution form. In the solution form, the A80407 antibiotic is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In other embodiments, this invention relates to (1) methods of improving feed-utilization efficiency in monogastric animals, such as poultry and swine, and in ruminants, such as sheep and cattle, (2) methods of promoting growth in animals such as poultry, swine, sheep and cattle raised for meat production and (3) methods of enhancing milk production in lactating ruminants. These methods comprise administering to the animal an amount of an A80407 antibiotic which is effective for the intended purpose.

For improving feed-utilization efficiency and promoting growth, an A80407 antibiotic is administered orally in a suitable feed in an amount of from about 2 to about 200 grams per ton of total feed. For beef cattle, for example, a range of about 12 to 1200 mg/head/day is suitable.

For enhancing milk production in lactating ruminants, oral administration of a daily amount of from about 0.04 to about 16 mg/kg of body weight (or about 25 to about 2500 mg/animal/day) is suggested.

In order to illustrate more fully the operation of this invention, the following examples are provided:

EXAMPLE 1

Preparation of Antibiotic A80407

A. Shake Flask Fermentation of A80407.4

The culture *Kibdelosporangium philippinensis* sp. nov. (NRRL 18199), either as a lyophilized pellet or as a suspension maintained under liquid nitrogen, is used to inoculate a seed medium with the following composition:

| SEED MEDIUM | |
|---|---|
| Ingredient | Amount (%) |
| Glucose | 1.0 |
| Soluble starch | 2.0 |
| Yeast extract | 0.5 |
| Enzyme-hydrolyzed casein* | 0.5 |
| CaCO$_3$ | 0.1 |
| NH$_4$H$_2$PO$_4$ | 0.1 |
| Deionized water | q.s. 1.0 liter |
| 5N NaOH was added to raise the pH of the medium to 7.0 prior to autoclaving. | |

*NZ Amine A, Sheffield Chemical Co., Norwich, NY

Slants or plates are prepared by adding 1.5% agar to the seed medium. The inoculated slant is incubated at 30° C. for 10 days. The mature slant culture is scraped with a sterile tool to loosen the spores and remove and macerate the mycelial mat. Approximately one-half of the loosened spores and culture growth thus obtained is used to inoculate 50 mL of a first-stage seed medium in a 250-mL wide-mouth Erlenmeyer flask.

The inoculated first-stage medium is incubated at 30° C. for 48 hours on a rotary shaker orbiting in a two-inch (5.08 cm) circle at 250 rpm.

This inoculated first-stage medium (1.0 mL) is used to inoculate 50 mL of a production medium having the following composition:

| Ingredient | Amount (%) |
|---|---|
| NH$_4$H$_2$PO$_4$ | 0.1 |
| Glycerol | 2.0 |
| CaCO$_3$ | 0.3 |
| MgSO$_4$.7H$_2$O | 0.05 |
| Yeast extract | 0.5 |
| Soybean flour* | 0.1 |
| Glucose | 0.5 |
| Deionized water | q.s. 1 liter |
| 5N NaOH is used to adjust the pH of the fermentation medium to 6.0 prior to autoclaving. | |

*Nutrisoy, Archer Daniels, Midland, MI

The inoculated fermentation medium is incubated in a 250-mL wide-mouth Erlenmeyer flask at 30° C. for 5 days on a rotary shaker orbiting in a two inch circle at 250 rpm.

B. Tank Fermentation of A80407.4 (100 Liters)

In order to provide a larger volume of inoculum, 10 mL of incubated first-stage medium, prepared as described in Section A, is used to inoculate 400 mL of a second-stage growth medium having the same composition as that of the first-stage medium. This second stage vegetative medium is incubated in a two-liter wide-mouth Erlenmeyer flask for 48 hours at 30° C. on a rotary shaker orbiting in a two-inch circle at 250 rpm.

Incubated second-stage vegetative medium (800 mL) thus prepared is used to inoculate 100 liters of sterile production medium, prepared as described in Section A. The inoculated medium is allowed to ferment in a 165-L stirred fermentation vessel for 120 hours at 30° C. The pH of the fermentation medium is maintained at 6.0 by adding 5N HCl as needed. Moderate airflow (0.5 v/v/m) and low rpm (200) in the stirred vessel maintain the dissolved oxygen level above 70% of air saturation.

C. Tank Fermentation of A80407.4 (1200 Gallons)

In order to generate even more material, the fermentation is carried out as in Sections A and B, but adapting the process to a 1600-gallon stirred vessel containing 1200 gallons of production medium. A large amount of second-stage medium (2.5 L) is used to inoculate 120 liters of seed medium in a 165-liter stirred vessel. The cells are grown for 48 hrs at 30° C. while being agitated at 200 rpm with an air flow of 1.2 cubic feet/min (CFM). This incubated seed medium (100 L) is used to inoculate 1200 gallons of production medium having the composition described in Section A.

The inoculated medium is allowed to ferment in a 1600-gallon stirred fermentation vessel for about 120 hours at 30° C. The pH of the fermentation medium is maintained at 6.0 by adding 2N HCl as required. An airflow of 30 CFM and slow agitation at 100 rpm in the stirred vessel maintains the dissolved oxygen level above 30% of air saturation.

EXAMPLE 2

Preparation of Antibiotic A80407 Using the A80407 Culture

*Kibdelosporangium philippinensis* sp. nov. NRRL 18198 is cultured, using the fermentation conditions described in Example 1, Sections A and B.

EXAMPLE 3

Isolation of Antibiotic A80407

Whole fermentation broth (4750 L) was obtained as described in Example 1, Section C. The pH of the broth was 5.9 [if the pH of the broth is above 6, it should be adjusted with glacial acetic acid to about pH 6]. The broth was filtered with the aid of 3% Celite 545 in a filter press. Diaion HP-20 resin (200 L) was added to the filtrate (4500 L), and the mixture was agitated for 2 hours. The spent filtrate was decanted, and the resin containing the A80407 was washed with water (1100 L) by stirring for 60 minutes. The washed resin was packed into a stainless-steel column. The resin column was washed with water (440 L) at a flow rate of 1 L per minute. The column was then developed with water-:acetonitrile (9:1) containing 0.5% acetic acid, collecting 50-L fractions and monitoring by analytical HPLC. Fractions containing A80407 (Nos. 10-11) were combined (100 L), concentrated in vacuo to a volume of 18 L and freeze-dried to yield 1486 g of antibiotic A80407.

EXAMPLE 4

Alternate Isolation of A80407

Whole broth (115 L, pH 5.6), obtained as described in Example 1, Section B, was filtered with the aid of Hyflo-Supercel. Diaion HP20 SS resin (5 L) was added to the filtrate (100 L), and the mixture was stirred for one hour. The spent filtrate was removed by decanting, and the resin was washed with water (20 L) and packed into a column. The resin column was washed with water and eluted sequentially with 10 L of water:isopropanol (9:1) containing 0.5% $H_3PO_4$, and 25 L of water:isopropanol (4:1) containing 0.5% $H_3PO_4$, collecting 1-L fractions and monitoring the elution by analytical HPLC. Fractions containing A80407 (Nos. 7-9) were combined (pH 2.7). Sufficient IRA-68 ($OH^-$) resin was added to bring the pH of the combined fractions to 5.7. The supernate was removed by decanting, concentrated in vacuo to a volume of 2 L and freeze-dried to yield 29 g of antibiotic A80407. This material contained about 88% A80407B.

EXAMPLE 5

Separation of A80407A and A80407B

Antibiotic A80407 (15 g), obtained as described in Example 3, was dissolved in water (50 mL) and applied to a stainless-steel column containing 5 L of YMC-C-8 (YMC Inc, Mt. Freedom, N. J. 07970) in 1.0% acetic acid. The column was developed with a gradient of 1.0% acetic acid to 6% acetonitrile in 1.0% acetic acid (starting with 11 L of each solvent) under a pressure of 600 psi. After 2 L was collected and discarded, 400-mL fractions were collected at a flow rate of 65 mL/min. Isolation was monitored by UV at 254 nm. Fractions containing A80407 components were assayed by HPLC. Fractions containing A80407A (Nos. 40-42) were combined, concentrated in vacuo and freeze-dried to yield 960 mg of highly purified A80407A. Fractions containing A80407B (Nos. 46-60) were combined, concentrated in vacuo and freeze-dried to yield 5.54 g of highly purified A80407B.

$C_{18}$ resins can be used instead of $C_8$ resins with good results.

EXAMPLE 6

Analytical HPLC System for A80407 Components

Column: Zorbax C8 (4.6×15 mm)
Detection: 235 nm, LDC detector, 1.0 AUFS
Solvent system: 8% acetonitrile in triethylamine buffer*, pH3.
Flow rate: 1.2 mL/minute
* 1 L water, 15 mL triethylamine, adjusted to pH 3 with conc. $H_3PO_4$ Using this system, the A80407 components have the following approximate retention times:

| Compound | Retention time (minutes) |
|---|---|
| A80407A | 2.89 |
| A80407B | 4.02 |

EXAMPLE 7

Preparation of A80407 Salts

The A80407 component is dissolved in deionized water. The pH of this solution is adjusted to about pH 3, using 0.5N acid (e.g., HCl, $H_2SO_4$, $H_3PO_4$). The solution is lyophilized to give the appropriate salt form.

EXAMPLE 8

A80407A Tablet Formulation

Tablets containing A80407A can be prepared using the following ingredients and amounts:

| Ingredient | Weight |
|---|---|
| A80407A phosphate | 282.9 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 mL |

Add A80407A phosphate, a portion of the microcrystalline cellulose and a portion of the croscarmellose sodium to a suitable container and blend until homogenous. Prepare a solution of Povidone in water, and add the Povidone solution to the blended powders. Granulate the resulting mixture, size if necessary and dry. Add the remaining microcrystalline cellulose and croscarmellose sodium to the dried mixture and blend. Add magnesium stearate and stearic acid, and blend the mixture. Compress the resulting powder blend into tablets.

EXAMPLE 9

A80407B Capsule Formulation

Capsules containing A80407B can be prepared using the following ingredients and amounts:

| Ingredient | Weight |
|---|---|
| A80407B hydrochloride | 262.2 mg |
| Corn starch flowable powder | 137.7 mg |
| Silicone fluid 350 centistokes | 2.7 mg |
| Corn starch | 147.1 mg |

Blend A80407B hydrochloride, starch flowable powder, silicone fluid 350 centistokes and starch powder in a suitable mixer until homogeneous. Fill into appropriate size hard gelatin capsules.

EXAMPLE 10

A80407A Suspension Formulation

Prepare a sterile insoluble form of A80407A by crystallization or precipitation. Mill or screen to a particle size suitable for suspension. Suspend the A80407A in the following vehicle.

| Ingredient | Amount |
|---|---|
| Lecithin | 1% |
| Sodium citrate | 2% |
| Propylparaben | 0.015% |
| Water for Injection | q.s. to desired volume |

The suspension may be manufactured in bulk and filled into vials or may be prepared extemporaneously by adding the vehicle to the A80407A in the vial.

EXAMPLE 11

A80407 Modified Chick Ration

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| A80407 (Sulfate Salt) | 0.01 | 0.2 |

These substances are mixed in accordance with standard feed-mixing techniques and fed to chicks with water ad libitum.

EXAMPLE 12

A80407-Improved Beef-Cattle Ration

A balanced high-grain beef-cattle ratio is prepared as follow:

| Ingredient | % | lbs |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A80407 (HCl salt) | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and $D_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g of soybean feed with 1% oil added
**Corn distillers dried grains with solubles containing 20,000 I.U. of d-alpha-tocopheryl acetate per pound The mixed feed is compressed into pellets.

EXAMPLE 13

A80407-Improved Swine Ration

A balanced swine farrowing ration is prepared as follows:

| Ingredient | % | lbs/ton |
|---|---|---|
| Ground yellow corn | 65.10 | 1302 |
| Soybean oil meal, solvent extracted dehulled | 18.50 | 370 |
| Dried-beet pulp | 10.00 | 200 |
| Dicalcium phosphate | 2.90 | 58 |
| Calcium carbonate | 1.20 | 24 |
| Swine vitamin premix[1] | 1.10 | 22 |
| Salt (NaCl) | 0.55 | 11 |
| Choline chloride, 25% | 0.35 | 7 |
| Trace-mineral premix[2] | 0.15 | 3 |
| Vitamin A premix[3] | 0.10 | 2 |
| Hydroxy analog of Methionine | 0.05 | 1 |
| Total | 100.00 | 2000 |

[1]Each kg of premix contains the following: 77,161 USP units Vitamin $D_2$; 2,205 I.U. of Vitamin E; 441 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; 22 mg biotin.
[2]Each kg of premix contains the following: 50 g of manganese as manganese sulfate; 100 g of zinc as zinc carbonate; 50 g of iron as ferrous sulfate; 5 g of copper as copper oxide; 1.5 g of iodine as potassium iodide and 150 g maximum and 130 g minimum calcium as calcium carbonate.
[3]Each kg of premix contains 6,6138.00 USP units Vitamin A.

For 200 pounds of this ration, a premix is prepared by adding A80407 (10 g) to a small amount of solvent-extracted soybean feed, grinding them in a mortar and pestle, and diluting the ground mixture to one pound with additional solvent-extracted soybean feed. This premix is then added to 200 lb. of the above-described swine ration, mixing by standard techniques. This feed provides a level of 100 grams of A80407 per ton of basal ration.

Larger or smaller quantities of ration with varying levels of A80407 are prepared by varying the quantity of A80407 in the premix and/or the quantity of basal ration.

Swine are fed at rates of from 1.0 to 10 grams of A80407 per 100 pounds of feed. Usually, swine consume about 6-8 lb of ration per day.

EXAMPLE 14

A80407-Formulation for Piglets

A80407 is dissolved in a small amount of ethanol. This ethanol solution is suspended in polyethylene glycol 200. The suspension is concentrated so that each unit dose has a volume of about 0.5 to 2 mL. Such suspensions are given to young pigs at rates of 0.5 to 50 mg per lb, three times a day by gavage.

We claim:

1. A process for producing antibiotic A80407 which comprises cultivating *Kibdelosporangium philippinensis* NRRL 18198 or NRRL 18199, or an A80407-producing mutant thereof, in a culture medium containing assimilable sources of carbon, nitrogen, and inorganic assimilable sources of carbon, nitrogen, and inorganic salts under submerged aerobic fermentation conditions until a recoverable amount of antibiotic A80407 is produced, and separating antibiotic A80407 from the culture medium.

2. The process of claim 1 which includes the additional step of separating component A80407A or component A80407B from antibiotic A80407.

3. The process of claim 1 wherein *K. philippinensis* NRRL 18198 is used.

4. The process of claim 1 wherein *K. philippinensis* NRRL 18199 is used.

5. A biologically purified culture selected from *Kibdelosporangium philippinensis* NRRL 18198 and NRRL 18199,, or an A80407-producing mutant thereof.

6. The culture of claim 5 which is *K. philippinensis* NRRL 18198 or an A80407-producing mutant thereof.

7. The culture of claim 6 which is *K. philippinensis* NRRL 18198.

8. The culture of claim 5 which is *K. philippinensis* NRRL 18199 or an A80407-producing mutant thereof.

9. The culture of claim 8 which is *K. philippinensis* NRRL 18199.

* * * * *